(12) United States Patent
Coffin, IV et al.

(10) Patent No.: US 6,184,521 B1
(45) Date of Patent: Feb. 6, 2001

(54) PHOTODIODE DETECTOR WITH INTEGRATED NOISE SHIELDING

(75) Inventors: James P. Coffin, IV, Trabuco Canyon, CA (US); Thomas J. Gerhardt, Littleton, CO (US); Michael A. Mills, Mission Viejo; Massi E. Kiani, Laguna Niguel, both of CA (US)

(73) Assignee: Masimo Corporation, Irvine, CA (US)

(*) Notice: Under 35 U.S.C. 154(b), the term of this patent shall be extended for 0 days.

(21) Appl. No.: 09/003,224

(22) Filed: Jan. 6, 1998

(51) Int. Cl.[7] ....................................................... H01J 3/14
(52) U.S. Cl. ...................... 250/237 R; 250/551; 250/216
(58) Field of Search ................................ 250/237 R, 239, 250/551, 226, 216; 356/41; 600/322, 344

(56) References Cited

U.S. PATENT DOCUMENTS

| | | | |
|---|---|---|---|
| 3,967,255 | 6/1976 | Oliver et al. | 169/61 |
| 3,973,118 | 8/1976 | LaMontagne | 250/226 |
| 4,303,855 | 12/1981 | Bapst et al. | 250/226 |
| 4,394,572 | * 7/1983 | Wilber | 250/239 |
| 4,407,290 | 10/1983 | Wilber | 600/330 |
| 4,633,087 | 12/1986 | Rosenthal et al. | 250/339.12 |
| 4,678,921 | * 7/1987 | Nakamura et al. | 250/574 |
| 4,864,126 | 9/1989 | Walters et al. | 250/551 |
| 4,865,038 | * 9/1989 | Rich et al. | 600/344 |
| 4,907,594 | 3/1990 | Muz | 600/335 |
| 4,939,375 | 7/1990 | Walters et al. | 250/551 |
| 5,036,437 | 7/1991 | Macks | 362/465 |
| 5,209,230 | * 5/1993 | Swedlow et al. | 600/322 |
| 5,237,994 | * 8/1993 | Goldberger | 600/323 |
| 5,239,169 | 8/1993 | Thomas | 235/462.06 |
| 5,325,192 | 6/1994 | Allen | 348/51 |
| 5,373,102 | 12/1994 | Ehrlich et al. | 174/35 R |
| 5,561,295 | * 10/1996 | Jacksen et al. | 250/338.4 |
| 5,629,517 | * 5/1997 | Jackson et al. | 250/208.1 |
| 5,752,914 | * 5/1998 | Delonzor et al. | 600/310 |
| 5,786,592 | * 7/1998 | Hok | 250/227.14 |

* cited by examiner

*Primary Examiner*—Que T. Le
*Assistant Examiner*—Thanh X. Luu
(74) *Attorney, Agent, or Firm*—Knobbe, Martens, Olson & Bear, LLP

(57) ABSTRACT

A photodiode has integrated shields for the rejection of noise-producing electromagnetic interference and ambient light. The electromagnetic shield forms a conductive matrix which covers the photodiode active area. The matrix is deposited as a metallization layer onto the photodiode and provides exposed portions of the active area for light detection. A pad is electrically connected to the shield to allow external termination of the shield. The ambient-light shield is in the form of a colored encapsulant surrounding the photodiode. The encapsulant provides a high-pass light transmission characteristic which passes signal light and rejects out-of-band ambient light. The photodiode is particularly advantageous for use in pulse oximetry probes.

5 Claims, 12 Drawing Sheets

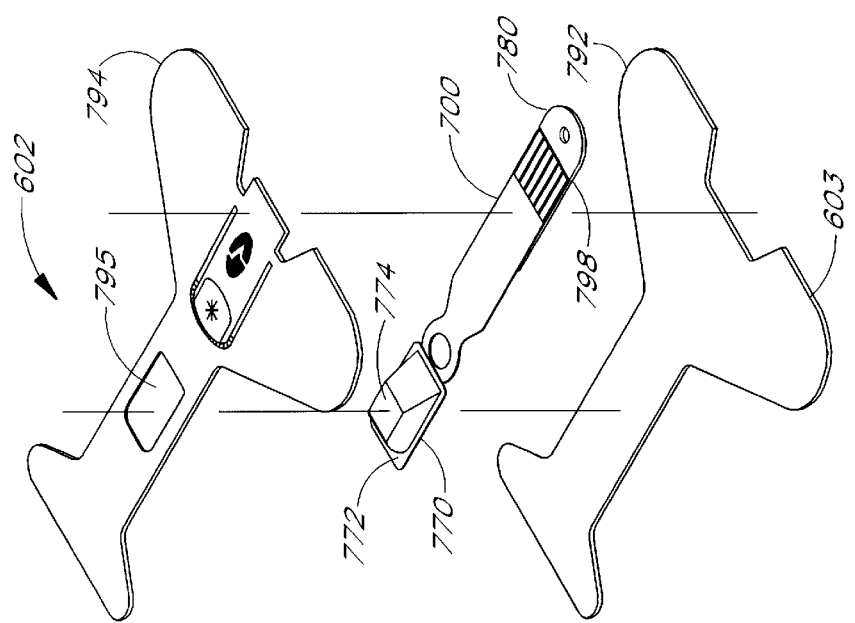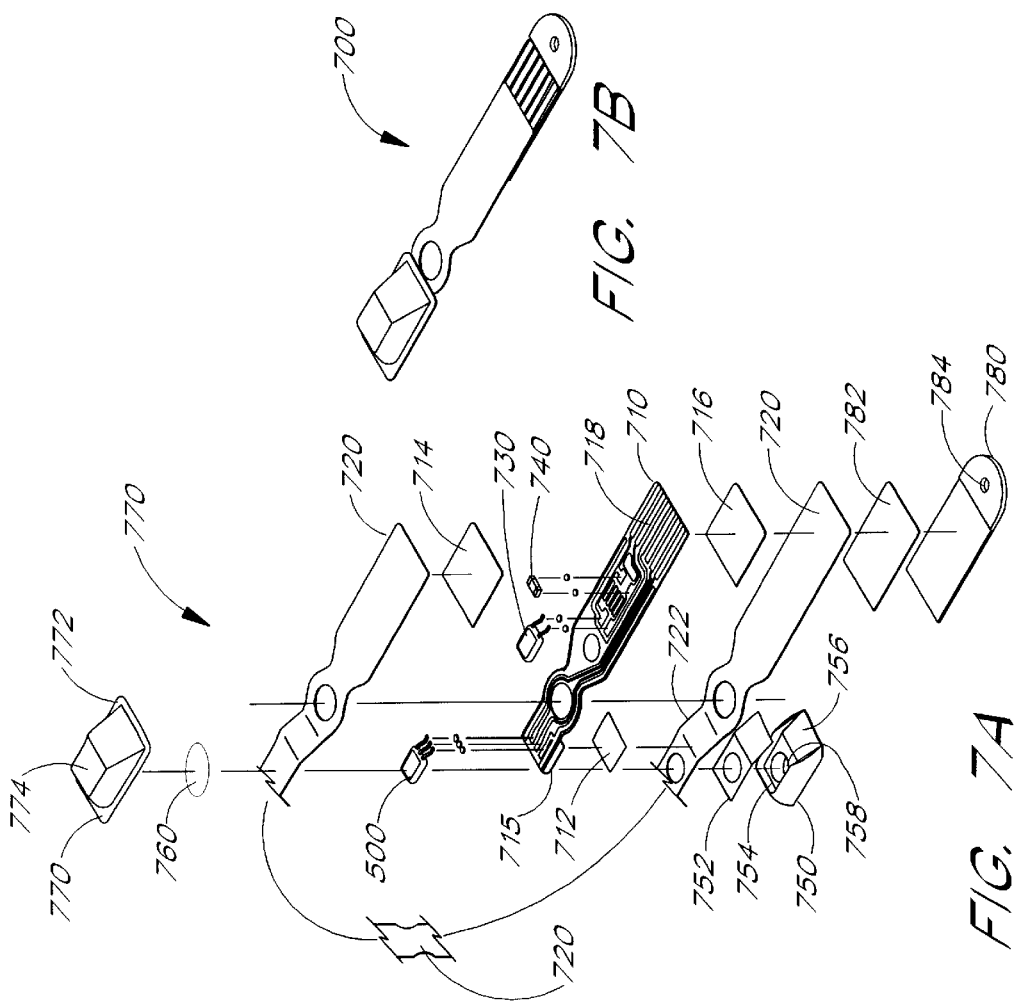

US 6,184,521 B1

PHOTODIODE DETECTOR WITH INTEGRATED NOISE SHIELDING

BACKGROUND OF THE INVENTION

1. Field of the Invention

This invention relates to the field of photodiode detectors, the field of electromagnetic interference and the field of band-limiting optics. In particular, this invention relates to electromagnetic and optical shielding to reduce background noise from photodiode detectors.

2. Description of the Related Art

A photodiode is a semiconductor device which converts the photon energy of light into an electrical signal by releasing and accelerating current-conducting carriers within the semiconductor. A photodiode behaves like an ordinary signal diode, but is specialized with respect to spectral response and efficiency to optimize internally generated current derived from illumination. In applications, a photodiode is often used as a detector which is optically coupled to a light-emitting-diode (LED) emitter. Examples of such applications include solid-state relays, remote control devices, optical communications and noninvasive biomedical sensors.

A limitation in many photodiode applications is a background noise floor which masks the signal detected by the photodiode. A contributing factor to background noise in a photodiode detector circuit, as in most electronic circuits, is the parasitic coupling of electromagnetic interference (EMI) into the circuit. External sources of EMI vary from power lines and cellular telephones to medical devices such as diathermy, MRI and lasers.

Conventionally, an electromagnetic shield is utilized as an effective method of reducing the effect of EMI-induced noise. Typical shielding techniques involve surrounding potentially affected parts with a "Faraday cage" of conducting material. However, conducting materials are typically opaque to optical signals. Hence, for photodiode applications, prior art electromagnetic shields have typically consisted of optically-transparent conductive materials, such as thin film silver or silver alloy or conductive "screens" having optically transmissive openings. This is illustrated in FIG. 1, which is a cut-away view of a prior art cage 100 containing an optical detector 110. The portions of the cage 100 within the optical path 140 between an emitter 150 and the detector 110 are constructed of a transparent or transmissive conductive material 120. The remainder of the cage 100 is conductive material 130 which may be opaque.

Besides electromagnetic interference, a contributing factor to background noise in photodiode detectors is ambient light. For photodiode applications, prior art ambient light reduction techniques typically consist of placing opaque, polarized or similar light-blocking material externally around the signal optical path and external wavelength filters within the signal optical path. This is illustrated in FIG. 2, which is a cut-away view of a prior art optical enclosure 200 containing an optical detector 110. The portion 220 of the enclosure 200 within the optical path 140 between an emitter 150 and the detector 110 is constructed of a wavelength filtering material. The remainder of the enclosure 200 is light blocking material 230.

SUMMARY OF THE INVENTION

A particularly advantageous application of a photodiode with integrated noise shielding according to the present invention is in pulse oximetry, and in particular, as a detector in pulse oximetry probes. Pulse oximetry is the noninvasive measurement of the oxygen saturation level of arterial blood. Early detection of low blood oxygen saturation is critical because an insufficient supply of oxygen can result in brain damage and death in a matter of minutes. The use of pulse oximetry in operating rooms and critical care settings is widely accepted.

A pulse oximetry probe is a sensor having a photodiode which detects light projected through a capillary bed by, typically, red and infrared LED emitters. The probe is attached to a finger, for example, and connected to an instrument which measures oxygen saturation by computing the differential absorption of these two light wavelengths after transmission through the finger. A probe may also be reflective, with the emitter and detector on the same side of vascularized tissue. This is sometimes referred to as "backscatter" oximetry. The LED emitters are alternately activated by the pulse oximetry instrument which then reads voltages indicating the resulting intensities ($I_{rd}$ and $I_{ir}$) detected by the photodiode, where $I_{rd}$ is the detected intensity of the red light and $I_{ir}$ is the detected intensity of the infrared light. A ratio of detected intensities is calculated and an arterial oxygen saturation value is empirically determined based on the ratio obtained:

$$I_{rd}/I_{ir} = \text{Ratio} \Rightarrow \% \ O_2 \text{ Saturation}$$

Unfortunately, pulse oximetry probes are adversely affected by background noise generated in the photodiode detector by both EMI and ambient light. EMI-generated noise enters an unshielded detector through parasitic capacitive coupling, i.e., through the mutual capacitances that exist between any two objects. Noise from ambient light is generated by the detector when light not generated by the emitters illuminates the photodiode. A significant portion of ambient light induced noise may result from light having wavelengths outside the emitter bandwidth but within the detector bandwidth.

The detector output from both signal and noise sources can be represented as:

$$I_{rd}/I_{ir} = (S_{rd}+N_{rd})/(S_{ir}+N_{ir})$$

where $S_{rd}$ is the signal component of the red light, $N_{rd}$ is the noise component of the red light, $S_{ir}$ is the signal component of the infrared light, and $N_{ir}$ is the noise component of the infrared light. If the noise level becomes large in relation to the signal, the ratio $I_{rd}/I_{ir}$ approaches 1, which corresponds to a false saturation reading of 85%. This noise problem is compounded by the critical human life mission of pulse oximetry devices. Thus, in pulse oximetry applications, there is a particular need for both EMI shielding and ambient-light shielding in order to increase the detector signal-to-noise ratio.

The use of conventional external noise shielding for photodiode detectors, including detectors used in pulse oximetry, has a number of drawbacks. Any practical external shielding enclosure includes openings which reduce shield effectiveness. For electromagnetic shields, shielding effectiveness (SE) can be expressed as $$SE = 20 \ \log(\lambda/2L)$$

where $\lambda$ is the interference wavelength and L the longest dimension of any opening. Thus, a mere ½ inch opening in a shield reduces shielding effectiveness beyond a minimally acceptable 20 db at frequencies as low as 1 GHz. Likewise for optical shields, small openings in opaque or wavelength filtering materials can allow noise-producing ambient light to reach the photodiode. This is particularly problematic for pulse oximetry probes, where the optical path from emitter to detector includes, for example, fingers and feet having a variety of sizes and shapes which frustrate achieving a light-tight seal.

In large-scale manufacturing applications, external shielding devices, both electromagnetic and optical, can add significantly to the cost of photodiode detectors, both in terms of additional parts and additional assembly steps. Conductive and optically transmissive shielding deposited directly on a photodiode substrate might overcome some limitations of external shielding but, generally, would require extra processing steps in photodiode fabrication, which would also increase final detector cost. A photodiode with integrated noise shielding according to the present invention is intended to eliminate or reduce these drawbacks encountered with conventional noise shielding techniques.

Another aspect of the present invention is a shielded detector which comprises a photodetector having an active area exposed to receive light. The photodetector is responsive to light of a first band of wavelengths. The shielded detector further comprises a shield deposited on at least portions of the exposed active area. In preferred embodiments, the shield comprises an electrically conductive layer deposited on at least portions of the exposed active area to provide an integrated electromagnetic shield for the photodetector. The shielded detector advantageously includes a pad portion, wherein the pad portion forms a part of the conductive layer. The shield has a low impedance path to the pad portion such that the pad portion forms an electrical path for connection to an external contact to permit external termination for the shield. In certain embodiments, the conductive layer comprises a metallization layer deposited directly on the portions of the exposed active area. The metallization layer comprises a grid which preferably forms the shield. The metallization layer also forms a second electrode for the detector. The second electrode is substantially electrically isolated from the shield. In preferred embodiments, the active area is responsive to the light of a first band of wavelengths, and the shield comprises an encapsulant covering at least the exposed active area. The encapsulant is substantially transparent to selected wavelengths within the first band of light wavelengths and is substantially attenuating to at least some other wavelengths within the first band of wavelengths. In particular embodiments, the other wavelengths within the first band of wavelengths are wavelengths below about 635 nanometers. Alternatively, the other wavelengths within the first band of wavelengths are wavelengths below about 350 nanometers. In a further alternative, the other wavelengths within the first band of wavelengths are wavelengths below about 500 nanometers. In certain preferred embodiments, the shield further comprises an optical filter which covers at least the exposed active area. The filter is substantially transparent to selected wavelengths within the first band of wavelengths and is substantially opaque to at least some other wavelengths within the first band of wavelengths. The filter advantageously comprises an encapsulant applied to the detector. The encapsulant preferably is in contact with and substantially covers the photodiode so as to form an integrated selective light filter for the photodiode. Preferably, the shielded detector further comprises an emitter which generates light of at least one selected wavelength within the first band of wavelengths. Also preferably, the photodetector comprises a generally planar photodiode, wherein the photodiode has first and second sides, the first side having the exposed active area and the second side having a first electrode for the photodiode. The shield preferably comprises a metallization layer deposited directly on at least a portion of the exposed active area. The metallization layer forms an electrically conductive grid and a second electrode for the photodiode. The second electrode is substantially electrically isolated from the grid. The shielded detector preferably includes a pad portion having a low impedance path to the grid, and the grid forms an integrated electromagnetic shield. The pad is adapted to be externally terminated through a conductor attached to the pad. Preferably, an optical filter material encapsulates the photodiode. The filter transmits light of at least selected wavelengths within the first band of wavelengths and attenuates at least some other wavelengths within the first band.

Another aspect of the present invention is a method of making a shielded detector having first and second sides. The method comprises the step of depositing a shield on an active area of a photodetector. Preferably, the step of depositing a shield comprises depositing a conductive grid and a shield pad for the conductive grid, wherein the active area is on the first side of the detector. The method preferably includes the further steps of depositing a first electrode for the detector on the first side and depositing a second electrode on the second side. Preferably, the grid is advantageously deposited in a pattern of cross-hatched traces disposed on exposed portions of the active area. The photodetector is mounted to provide a connection between the first and second electrodes of the photodiode with first and second electrode leads. The method preferably includes the step of bonding a first wire between the shield pad and a shield lead and the step of bonding a second wire between the electrode pad and the second electrode lead. Preferably, the active areas are responsive to light in a first band of wavelengths, and the method includes the further step of depositing an optical filter over the active area of the photodetector. The optical filter is preferably formed of an encapsulating material which substantially attenuates at least a first range of wavelengths within the first band of wavelengths and which transmits at least a second range of wavelengths within the first band of wavelengths.

Another aspect of the present invention is a shielded pulse oximetry probe which comprises a substrate and an emitter mounted to a first portion of the substrate. The emitter is configured to transmit light within a first band of wavelengths. A detector is mounted to a second portion of the substrate. The detector is responsive to wavelengths in the first band and to at least some wavelengths outside the first band. A shield, comprising an electromagnetic shield, is formed over the detector. Preferably, the shield further comprises an optical shield. The optical shield substantially attenuates at least a portion of the wavelengths to which the detector is responsive outside the first band and transmits at least selected wavelengths in the first band. The optical shield advantageously comprises an encapsulant which covers the detector. The photodetector preferably comprises a metallization layer, and the electromagnetic shield is preferably fabricated as an integral portion of the metallization layer.

Another aspect of the present invention is a photodiode detector having an integrated electromagnetic shield. The shield is a conductive layer deposited on covered portions of the photodiode active area which leaves exposed active area portions. A bonding pad is deposited as a portion of the shield to provide a low impedance path to substantially all of the shield. A conductor may be attached to the pad to provide an external shield termination. A particularly advantageous aspect of the invention is that the shield is formed during deposition of the conventional metallization layer which deposits a photodiode electrode. Thus, the shield is created by modification of a conventional metallization layer mask and requires little if any modification of the standard photodiode processing steps. Further, unlike external shields, the deposited shield requires no additional parts. An additional advantage of this integrated shield is its proximity to the photodiode component, which eliminates significant shield openings which might pass high frequency EMI.

Another aspect of this invention is a photodiode detector having an integrated ambient-light shield. The shield is an encapsulating material encasing the photodiode. The encapsulant has optical transmission characteristics which pass desired emitter wavelengths but filter other wavelengths that are within the response band of the detector. A particularly advantageous aspect of the integrated optical shield is that it is formed as a conventional encapsulant which protects the photodiode and retains the photodiode leads after separation from the lead frame. Thus, the shield is created by modification of the material used during a conventional encapsulation process and requires little, if any, modification to the standard photodiode fabrication steps. Further, the shield requires no additional parts, as with external shields. An additional advantage of this integrated shield is its proximity to the photodiode component, allowing for little if any ambient light leakage.

Another aspect of the present invention is a shielded detector which comprises a photodiode having an active area. An electrically conductive layer is deposited on covered portions of the active area and is disposed about exposed portions of the active area. The exposed portions are responsive to light. A pad portion of the conductive layer is connected by a low impedance path to substantially all of the conductive layer. The conductive layer forms an integrated electromagnetic shield for the photodiode which may be externally terminated through the pad portion.

Another aspect of the present invention is a shielded detector which comprises a photodiode responsive to a first band of wavelengths in optical communication with an emitter which produces a second band of wavelengths. At least a portion of the second band falls within the first band. A colored encapsulant is in contact with and substantially surrounds the photodiode. The encapsulant transmits wavelengths within the second band and blocks at least a portion of wavelengths outside the second band and within the first band. The encapsulant forms an integrated ambient-light shield for the photodiode.

Another aspect of the present invention is a shielded detector which comprises a generally planar photodiode having a first side and a second side. The first side has a first electrode, and the second side has an active area responsive to light within a first band of wavelengths. A metallization layer is deposited directly on the second side. The metallization layer comprises an electrically conductive grid and a second electrode. The second electrode is substantially electrically isolated from the grid. The grid is disposed around exposed portions of the active area. An emitter is operable to generate light within a second band of wavelengths. At least a portion of the second band is within the first band so that current is generated through the first and second electrodes when the exposed portions are in optical communications with the emitter. A pad portion of the grid has a low impedance path to substantially all of the grid, so that the grid functions as an integrated electromagnetic shield which may be externally terminated through a conductor attached to the pad. An optical filter material encapsulates the photodiode. The filter transmits light at wavelengths within the second band and blocks at least a portion of wavelengths within the first band and outside the second band. The filter material shields ambient light from the photodiode.

Another aspect of the present invention is a method of creating a shielded detector. The method comprises the step of depositing a metallization layer directly on an active area of a photodiode to form a conductive grid, a shield pad and an electrode pad. The grid is in a pattern of cross-hatched traces disposed around exposed portions of the active area. The method comprises the further steps of mounting the photodiode to provide a connection between an electrode portion of the photodiode and a first electrode lead; bonding a first wire between the shield pad and a shield lead; and bonding a second wire between the electrode pad and a second electrode lead. The method includes the further step of encapsulating the photodiode in an optically-transmissive material. Preferably, the optically-transmissive material has a filtering characteristic that attenuates light having wavelengths outside a desired frequency band to be detected.

Another aspect of the present invention is a shielded pulse oximetry probe which comprises a flexible circuit media. An emitter is mounted on a first portion of the media. The emitter is capable of transmitting light within a first frequency band. A detector is mounted on a second portion of the media. The detector comprises a photodiode and a surrounding encapsulant. The photodiode is at least partially responsive to light within the first frequency band. The media is configurable such that the detector is in optical communications with the emitter. A shield is fabricated as an integral portion of at least one of the photodiode metallization layer and the encapsulant. The shield reduces the amount of background noise in the detector.

Another aspect of the present invention is a photodiode which has integrated shields for the rejection of noise-producing electromagnetic interference and ambient light. The electromagnetic shield forms a conductive matrix which covers the photodiode active area. The matrix is deposited as a metallization layer onto the photodiode and provides exposed portions of the active area for light detection. A pad is electrically connected to the shield to allow external termination of the shield. The ambient-light shield is in the form of a colored encapsulant surrounding the photodiode. The encapsulant provides a high-pass light transmission characteristic which passes signal light and rejects out-of-band ambient light. The photodiode is particularly advantageous for use in pulse oximetry probes.

BRIEF DESCRIPTION OF THE DRAWINGS

The present invention will be described in detail below in connection with the following drawing figures in which:

FIGS. 7A, 7B and 7C are assembly diagrams of a pulse oximeter probe incorporating a photodiode detector having integrated noise shielding.

DETAILED DESCRIPTION OF THE PREFERRED EMBODIMENT

Figure 1:
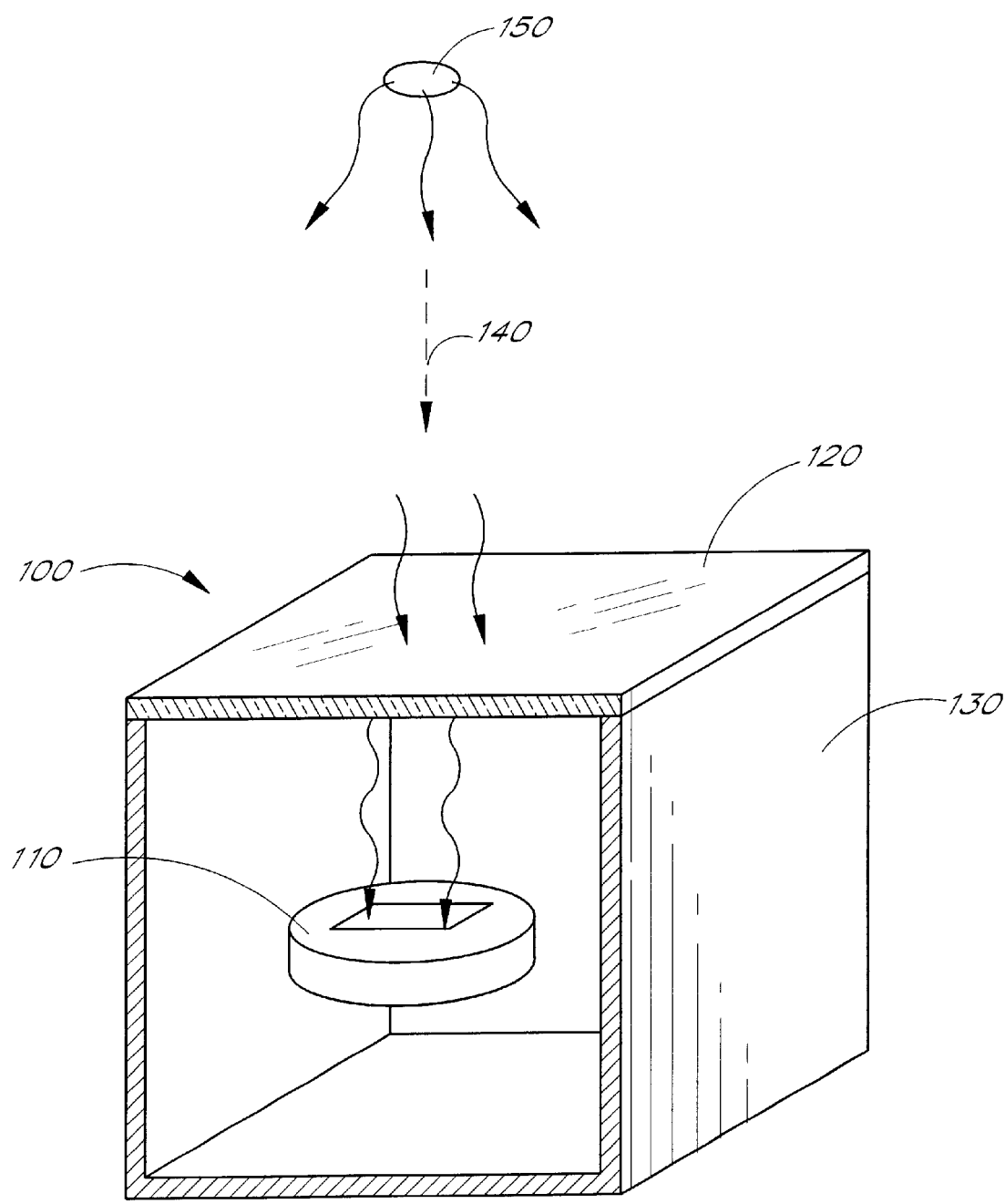
FIG. 1 is a cut-away view of a prior art "Faraday cage" external to a photodiode detector.
Figure 2:
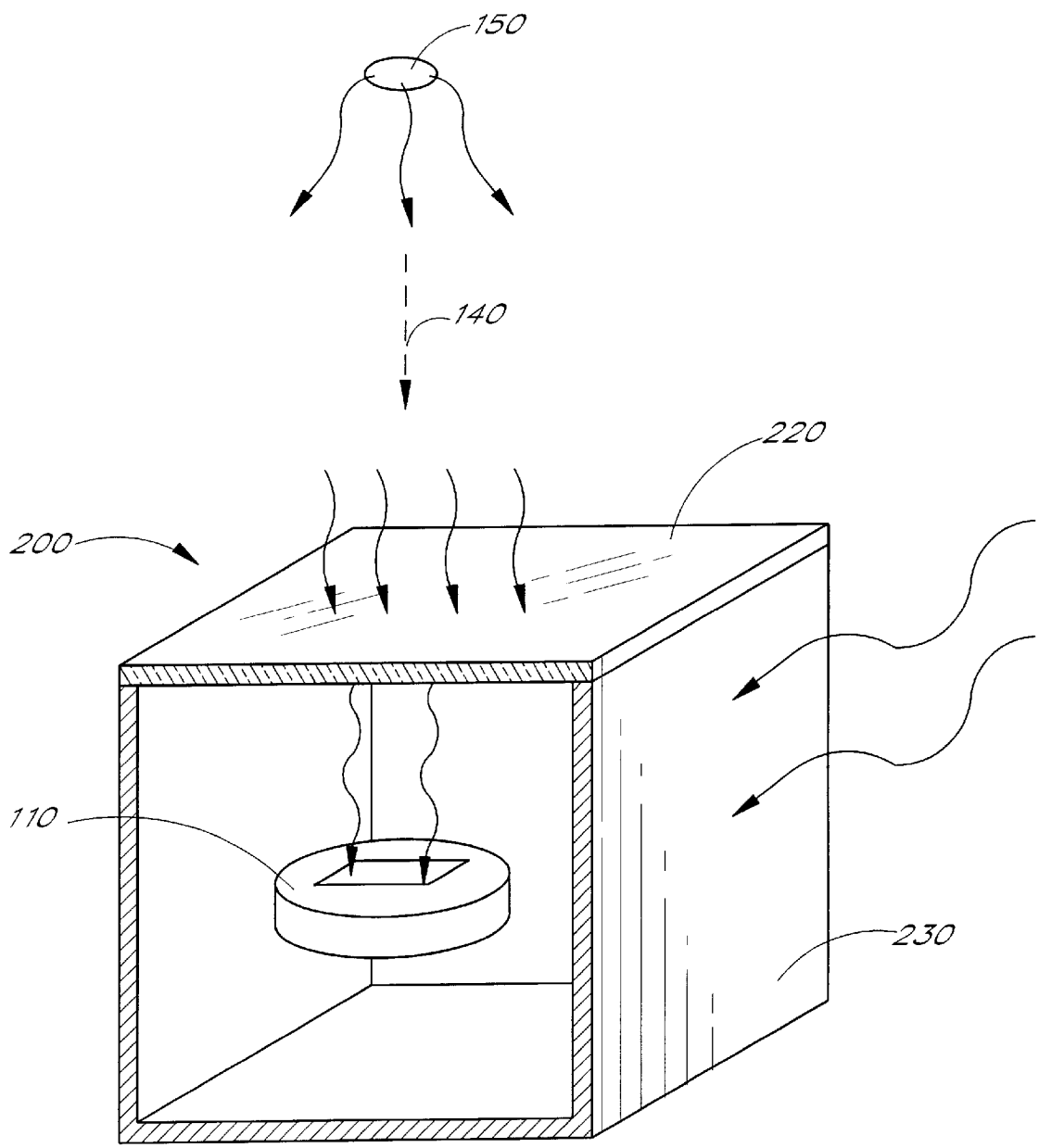
FIG. 2 is a cut-away view of prior art optical enclosure having blocking and wavelength filtering materials external to a photodiode detector.
Figure 3A:
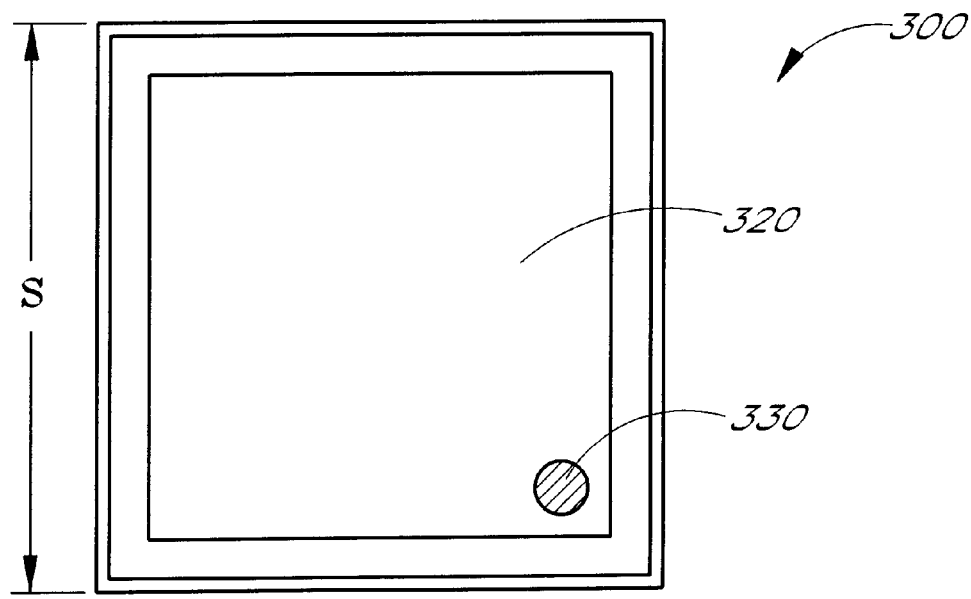
FIGS. 3A and 3B are layout views of a preferred unshielded photodiode chip used in constructing a photodiode with integrated shielding according to the present invention.
Figure 3B:
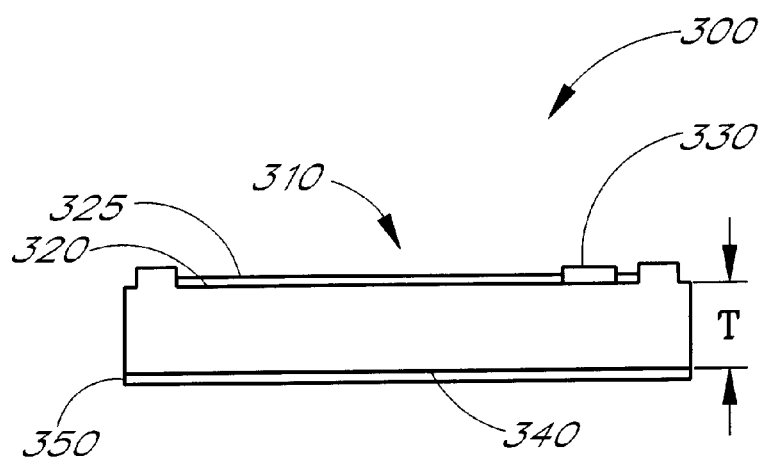

FIGS. 3A and 3B illustrate a preferred unshielded silicon photodiode chip used in constructing a photodiode detector with integrated noise shielding according to the present invention. The photodiode chip 300 is a planar device constructed of a layer of intrinsic-type semiconductor material sandwiched between layers of P-type and N-type semiconductor material, referred to as a PIN diode. The added intrinsic layer increases the spectral range of response of the photodiode by expanding the depletion region of the P-N junction, which then encompasses carriers released by a broader range of photon wavelengths.

A preferred photodiode chip is device number PD-0120C available from Opto Tech Corporation, Semiconductor Division, Hsinchu, Taiwan, R.O.C. This photodiode chip 300 is 125 mils (0.125 inch) on each side, S (FIG. 3A), and is 12±1.5 mils thick, T (FIG. 3B). The top side 310 of this diode 300 has an active area 320 of approximately 112×112 mils. An anti-reflective coating 325 covers the active area 320. An aluminum alloy anode bond pad 330 which is 8 mils in diameter is deposited as a metallization layer on the side 310 of the diode 300, preferably in one corner thereof. The back side 340 of the diode 300 has a deposited gold alloy cathode 350.

Figure 4A:
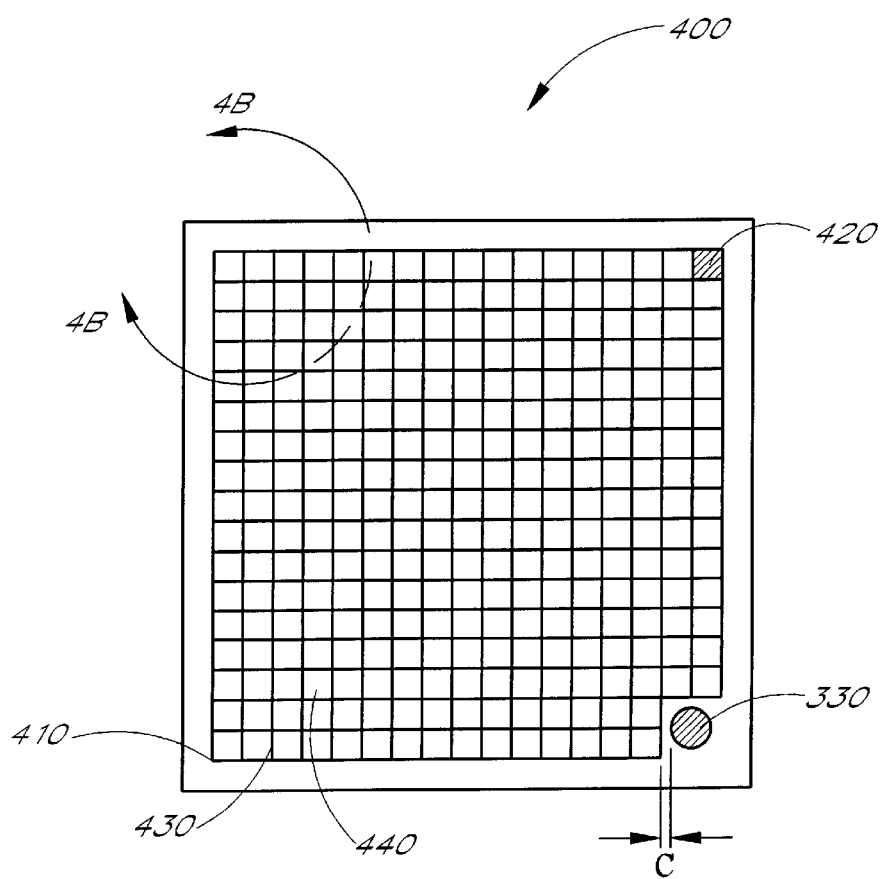
FIG. 4A is a layout view of a photodiode chip having a transmissive-grid metallization layer which forms an integrated electromagnetic shield.
Figure 4B:
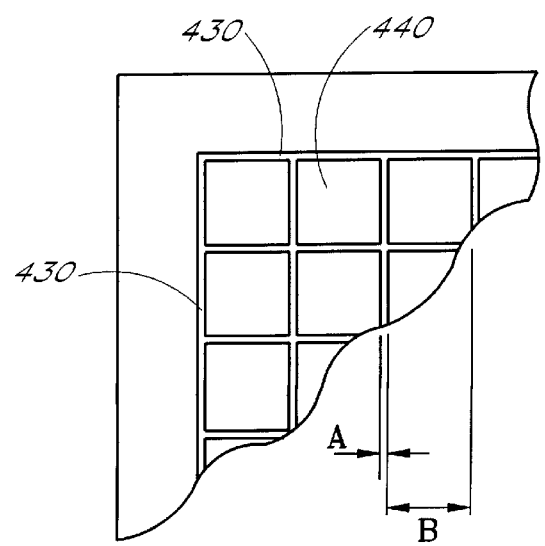
FIG. 4B is an enlarged view of a portion of the photodiode chip of FIG. 4A showing the relative spacing of the conductors forming the grid metallization layer.

FIG. 4 depicts an improved planar PIN photodiode chip 400 having a modified metallization layer which forms a conductive matrix 410 across the photodiode active area. This matrix performs as an integrated electromagnetic shield for the photodiode 400. Advantageously, the conductive matrix is deposited on the photodiode 400 during the same process step that deposits the photodiode anode bonding pad. Thus, no additional processing steps are required to create the shield layer as compared to the unshielded photodiode depicted in FIG. 3.

One shielding mechanism is the reflection of an incident electromagnetic wave by the shield surface. Reflection depends on an impedance mismatch between this incident wave and the reflecting shield surface. Shielding effectiveness (SE) is:

$$SE = 20 \cdot \log|Z_w/4 \cdot Z_s|$$

where $Z_w$ is the impedance of an incident wave and $Z_s$ is the impedance of the shield in ohms/square. Thus, an effective shield has a small $Z_s$, i.e., is highly conductive. At high frequencies, conductivity occurs only near the surface of the shield, due to skin effect. Skin depth is:

$$\delta = \sqrt{(2/2\pi f \mu \sigma)}$$

where f is frequency of the incident electromagnetic wave, $\mu$ is permeability of the shield material and $\sigma$ is conductivity of the shield material. Most of the current induced in a shield by an incident wave passes within one skin depth of the surface, and very little current goes deeper than three skin depths. Thus, above a few skin depths, the thickness of the shield material is of no consequence with respect to this reflective shielding mechanism.

Skin depths, in mils, of common shielding materials are:

| Frequency | Copper | Aluminum | Steel |
|---|---|---|---|
| 1 MHz | 3 | 3 | .3 |
| 10 MHz | .8 | 1 | .1 |
| 100 MHz | .26 | .3 | .08 |
| 1 GHz | .08 | .1 | .04 |

As further shown in FIG. 4, the shielding matrix of the current invention is preferably a grid composed of vacuum-sputtered aluminum traces 430. A preferred grid pattern is a right-angled, crisscross pattern which creates alternate portions 440 of square-shaped exposed active area and metallized active area, as shown in FIG. 4. A shield bond pad 420 is located at one corner of the grid 410. All of the grid traces are interconnected with each other and with the shield bond pad 420. Thus, an electrical connection between the bond pad and a lead allows the entire grid 410 to be grounded via this lead. The anode bond pad 330, is electrically isolated from the grid 410.

There is a tradeoff between shield effectiveness and detector signal strength which is a function of the amount of photodiode active area which is covered by the shield grid 410. At one extreme, if the shield is solid, $Z_s$ is minimized and, therefore, shield effectiveness is maximized, but only minimal, if any, light can reach the photodiode. At the other extreme, the shield grid lines are thin and widely spaced, maximizing the exposed photodiode active area but decreasing shield conductivity and, hence, effectiveness. In a preferred embodiment, the effective active area of the photodiode, i.e., the active area of the photodiode which is exposed to light, is between 80% to 90% of the actual photodiode active area. That is, 80% to 90% of the photodiode active area is exposed to light. However, any coverage percentage which permits sufficient light to pass and still provide acceptable signal strength will also work.

One embodiment of the shield grid is dimensioned approximately 112 mils×112 mils (i.e., located over and coextensive with the active area 320 of the photodiode. As illustrated in the enlarged detail in FIG. 4A, each conductive trace has a width, A, which, in the preferred embodiment is approximately 0.55 mils. The traces are spaced apart by a spacing distance, B, which, in the preferred embodiment, is approximately 6 mils. As shown in FIG. 4A, a clearance distance, C, is provided between the anode bond pad 330 and the grid 410. The distance C is approximately 3 mils in the preferred embodiment. The anode bond pad 330 is circular and is approximately 8 mils in diameter. The shield bond pad 420 is square and is approximately 8 mils per side. The metallized active area, being optically opaque, is not part of the effective active area of the shielded photodiode. With the foregoing dimensions, the approximate effective active area of the photodiode can be computed as follows:

[1] Total Active Area=$112^2$

[2] Total Area of Horizontal Metallization Lines=18×[17×(6+0.55)+0.55]×0.55

[3] Total Area of Vertical Line Segments=18×[17×6×0.55]

[4] Total Area of Removed Horizontal Line Segments= 2×[2×(6+0.55)×0.55]

[5] Total Area of Removed Vertical Line Segments=4× [6×0.55]

[6] Area of Anode Bond Pad=$\pi \times 4^2$

[7] Area of Filled Inner Square of Shield Bond Pad=$6^2$

Percent of Area Covered By Metallization=([2]+[3]−[4]−[5]+[6]+[7])/[1]=(1107.81+1009.8−14.41−13.2+36+50.26)/12544=17.34%

Thus, the embodiment described above has an effective active area which is approximately 82.66% of the actual active area of the photodiode.

Figure 5A:
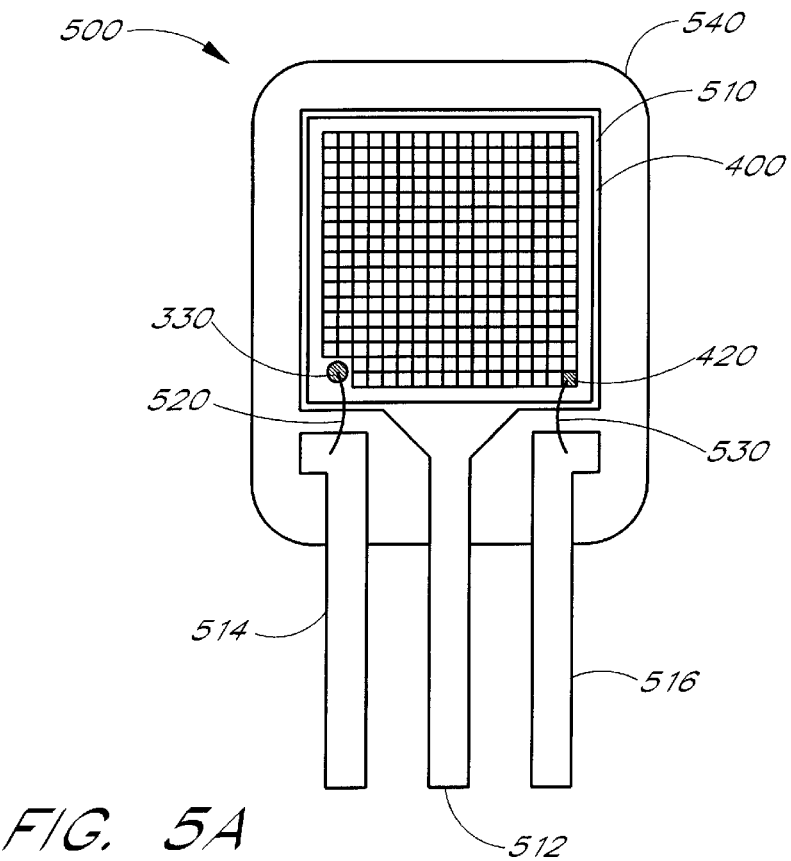
FIGS. 5A and 5B illustrate a detector incorporating an encapsulated, shielded photodiode chip.
Figure 5B:
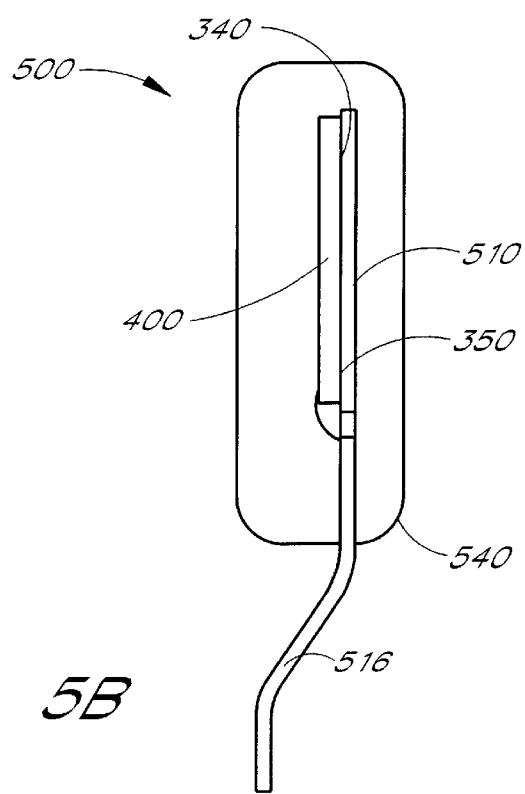

FIGS. 5A and 5B show the photodiode with integrated electromagnetic shield 400 packaged so as to form an encapsulated, leaded detector 500. The chip 400 is attached to a leadframe 510 with conductive adhesive applied between the cathode side 340 of the chip 400 and the leadframe 510. This makes an electrical connection between the photodiode cathode 350 and one lead 512 of the leadframe. An anode wire connection 520 is made between the chip anode bond pad 330 and another lead 514 of the leadframe 510. A shield wire connection 530 is made between the shield bond pad 420 and a third lead 516 of the leadframe 510. Preferably, the wire connections to the anode bond pad 330 and the shield bond pad 420 are gold wires. A ball bond is created on the anode bond pad 330 or the shield bond pad 420 of the diode 400, and a stitch bond is formed on the respective lead of the leadframe 510. The anode and shield wire connections may also be made with aluminum, copper or similar metals, and the connections can be wedge bonded. Other interconnection methods, such as TAB or flip-chip, can also be used. This detector assembly is then placed in a transfer mold which is filled with an epoxy molding compound. Other potential methods for encapsulation include pour molding, injection molding, or the dispensing of a material in liquid form which subsequently cures via a chemical reaction, the addition of heat, or exposure to radiant energy. A preferred epoxy molding compound is HYSOL® MG18, which is available from The Dexter Corporation, Electronic Materials Division, Industry, Calif. The epoxy compound is cured and deflashed to create an encapsulation 540. The leadframe 510 is then trimmed and the leads are formed to complete the detector 500.

Figure 5C:
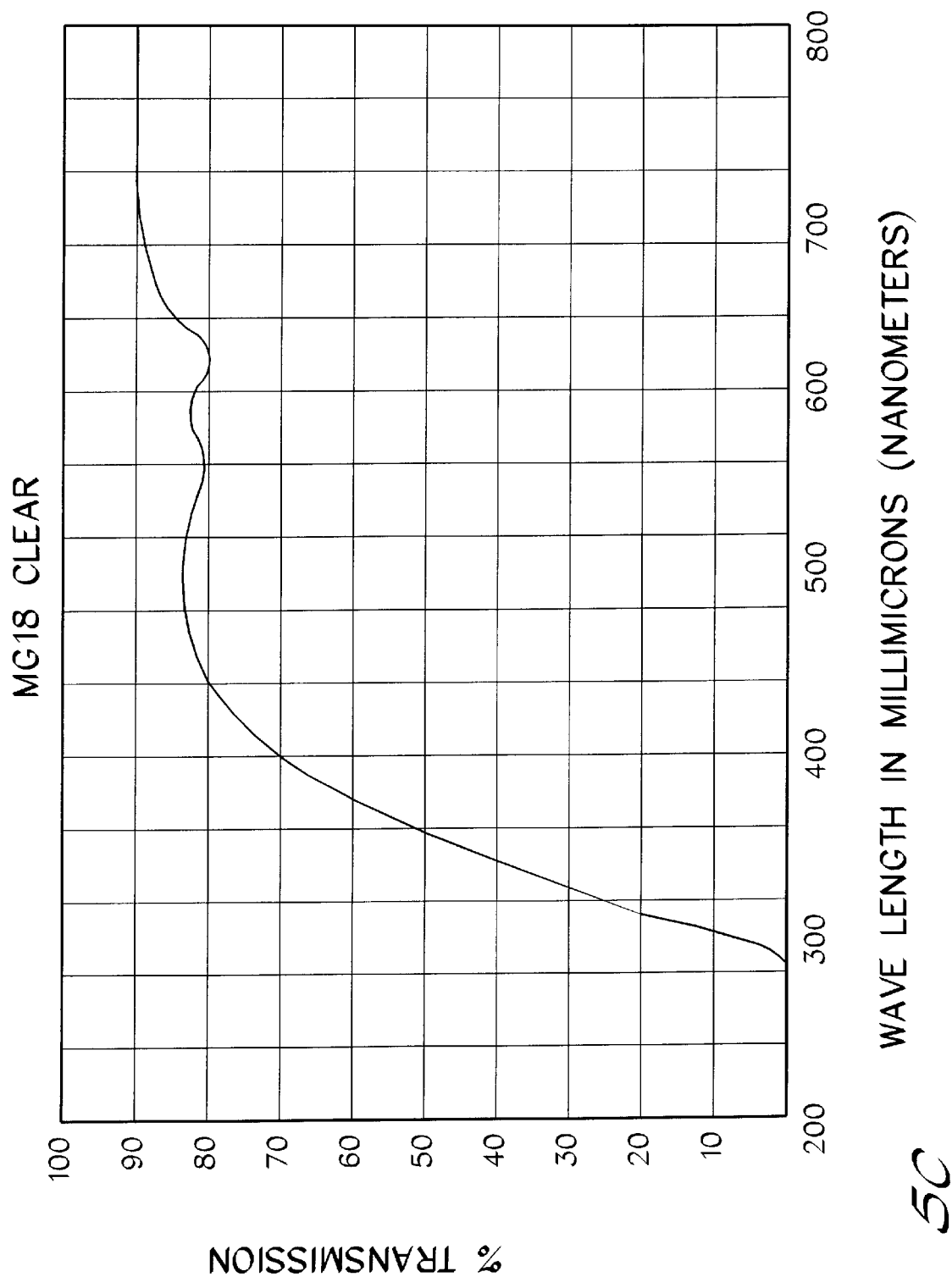
FIGS. 5C, 5D and 5E depict the light transmission characteristics for clear and colored encapsulating material.
Figure 5D:
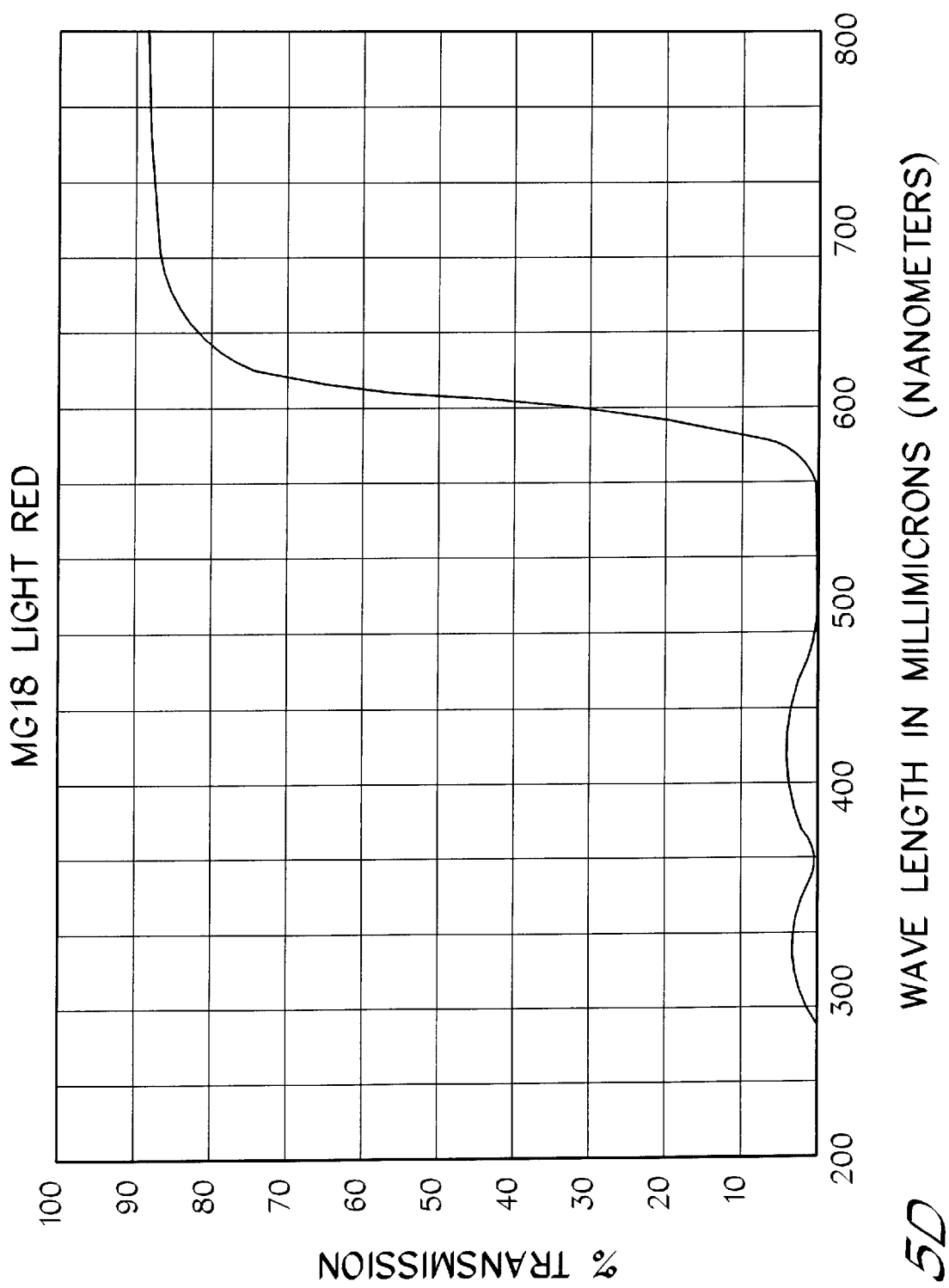
Figure 5E:
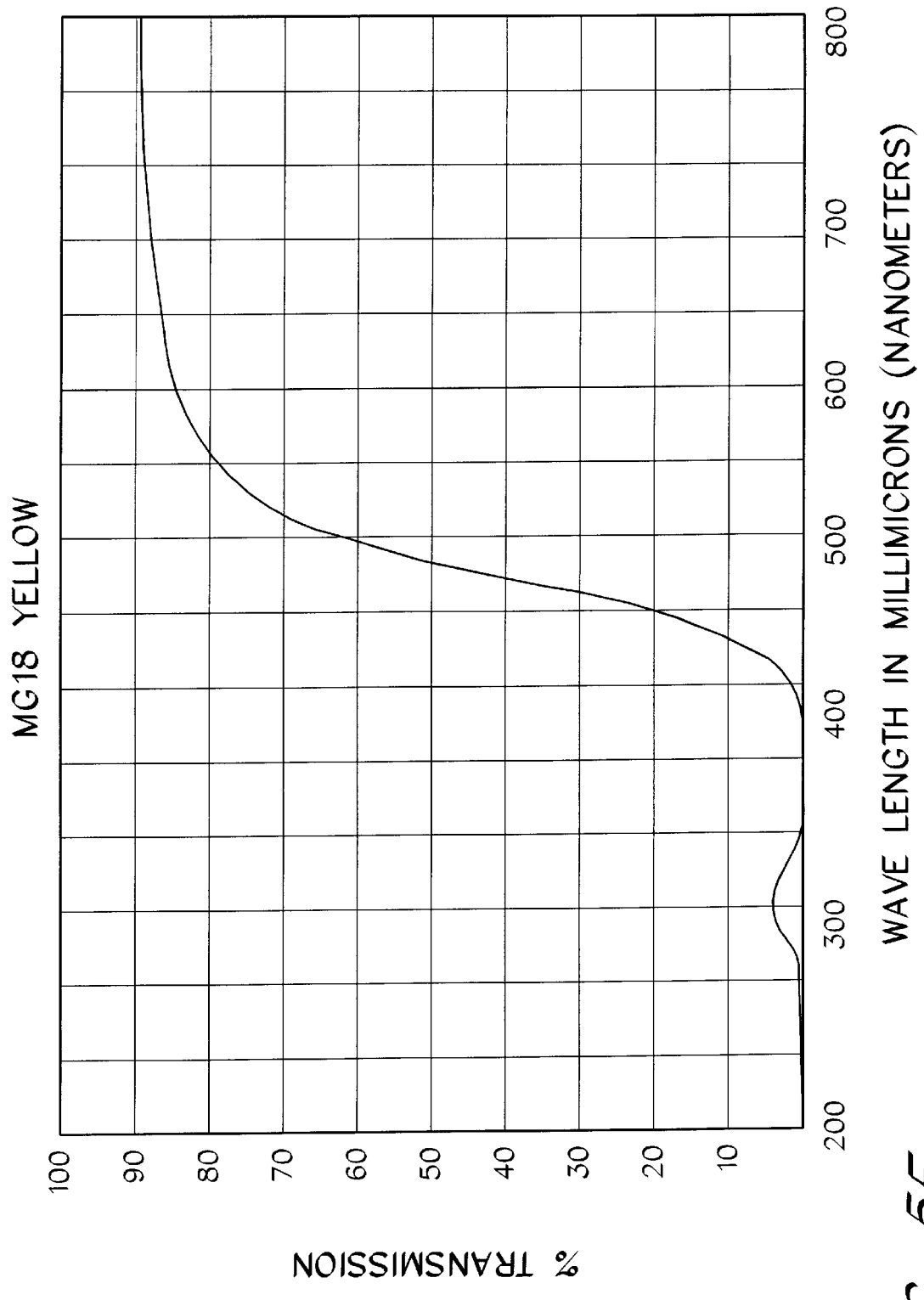

As shown in FIGS. 5C, 5D and 5E, the MG18 encapsulant 540 can be purchased clear or in various colors, including light red and yellow. A colored encapsulant can advantageously be used as an integrated, ambient-light shield for a photodiode detector in applications where the signal of interest is within the passband of the color encapsulant and interfering ambient light is outside this passband. One such application is pulse oximetry, as described above.

Figure 6A:
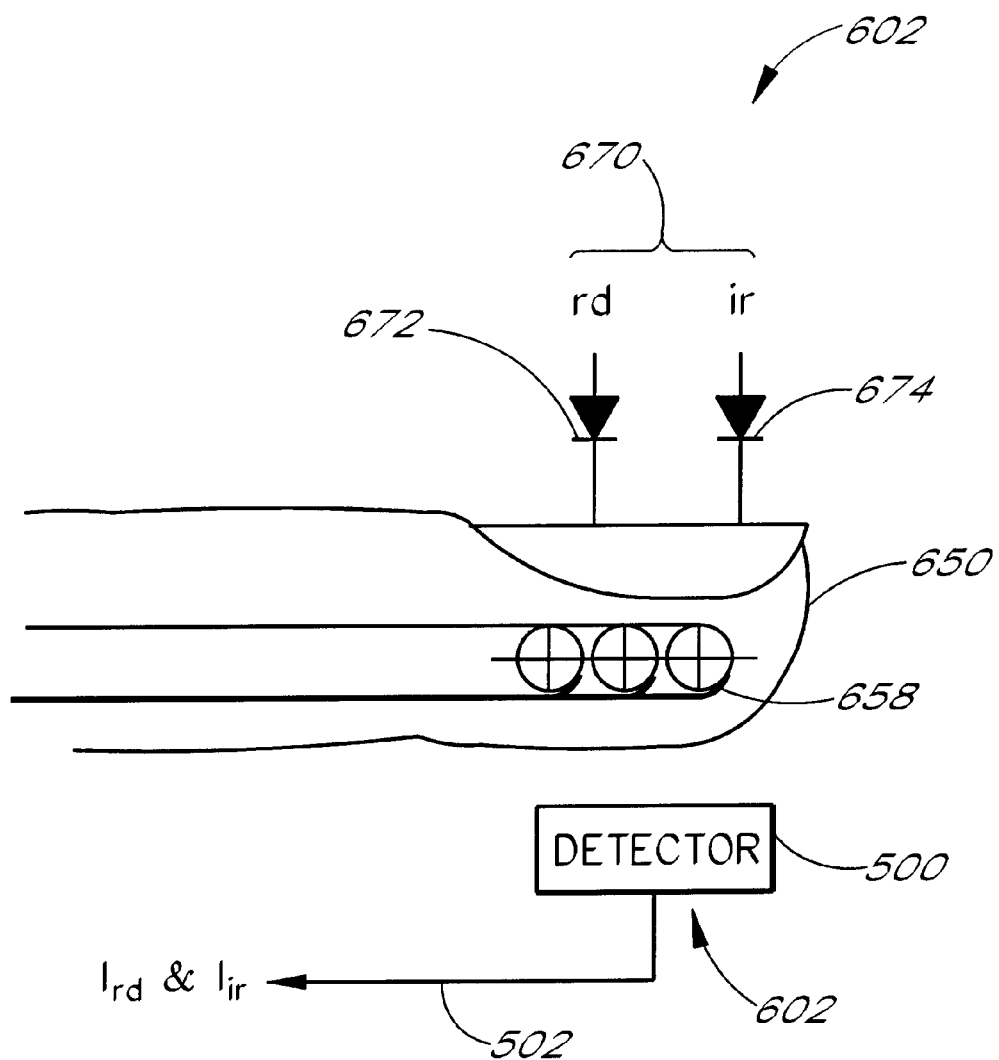
FIG. 6A illustrates a photodiode detector used in a pulse oximetry probe.

As depicted in FIG. 6A, a pulse oximetry probe 602 can be attached to a finger 650, for example, to project light through a capillary bed 658. In a particular embodiment of the pulse oximetry probe 602, the red LED 672 of the emitter 670 produces light centered at 660 nanometers with a bandwidth of 50 nanometers, i.e., light having wavelengths from 635 nanometers to 685 nanometers. The infrared LED 674 of the emitter 670 produces light centered at 905 nanometers. However, the photodiode detector 500 is sensitive to wavelengths as small as 450 nanometers. Thus, with the clear encapsulant shown in FIG. 5C, the detector 500 will be responsive to noise-producing ambient light which is entirely outside the band of light produced by the red LED 672, specifically light having wavelengths in the range 450–635 nanometers. Hence, for pulse oximetry applications, a preferred encapsulant is an encapsulant which absorbs light having wavelengths in the range of 450 nanometers to 635 nanometers and which transmits light having wavelengths greater than 635 nanometers. Exemplary encapsulants meeting this criteria are the MG18 light red and the MG18 yellow epoxy molding compounds, having the transmission characteristics shown in FIG. 5D and FIG. 5E, respectively. A most preferred encapsulant for a pulse oximetry probe 602 is the MG18 light red epoxy molding compound, having a cutoff very close to 635 nanometers (i.e., which attenuates light having wavelengths less than approximately 635 nanometers).

Figure 6B:
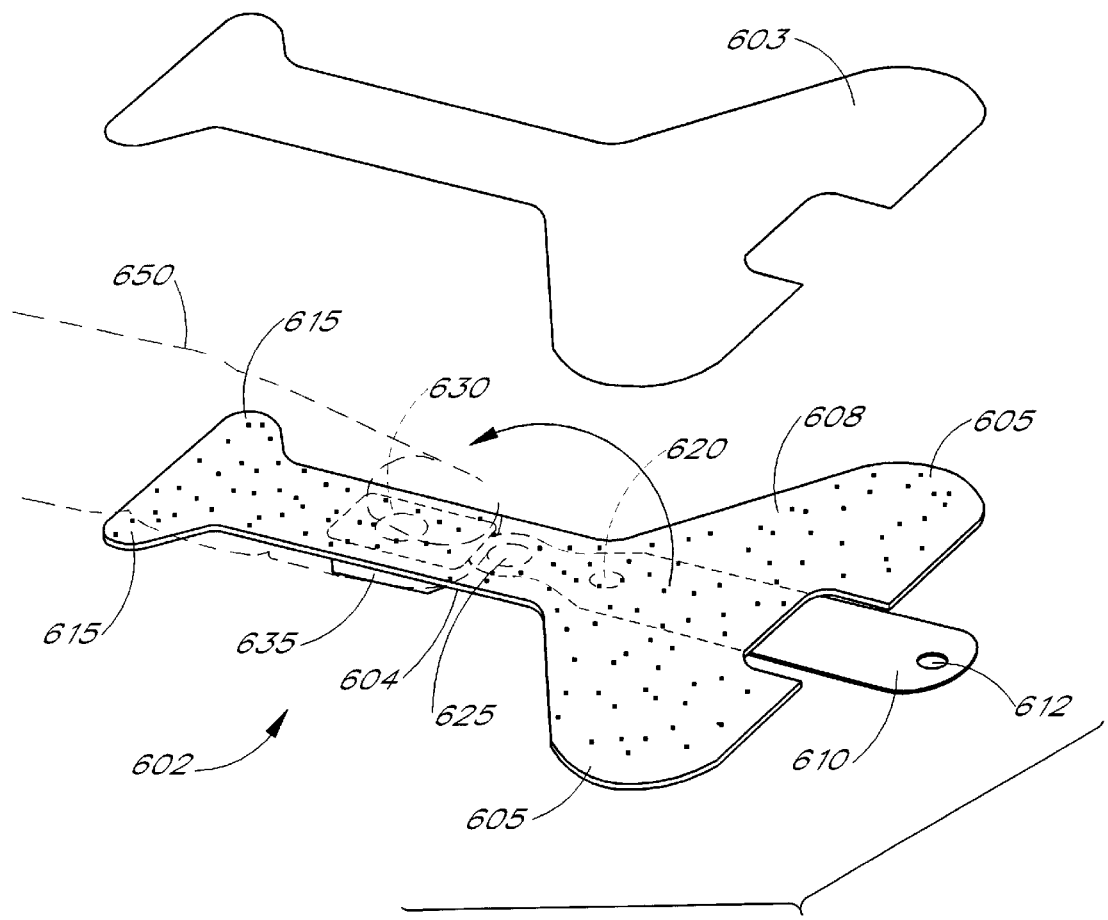
FIGS. 6B and 6C depict a pulse oximeter probe incorporating a photodiode detector having integrated noise shielding.
Figure 6C:
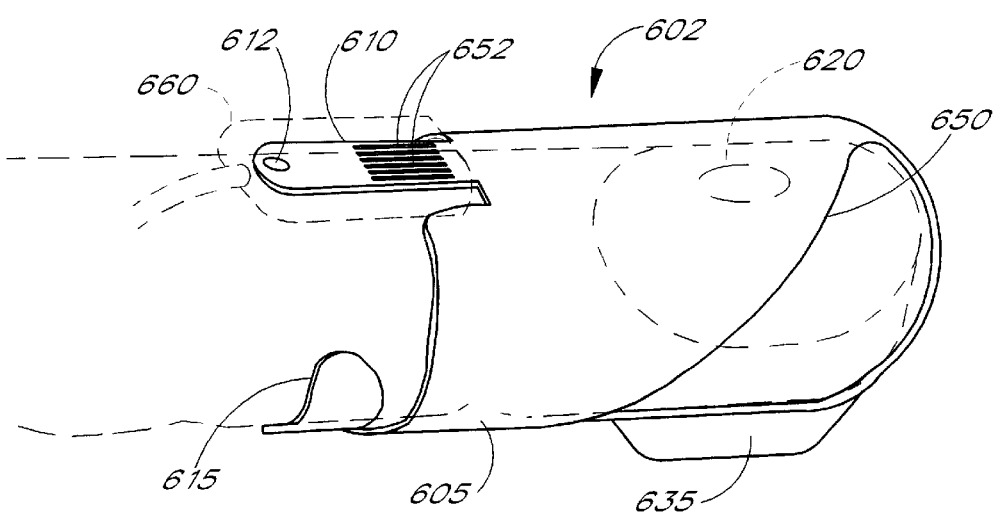

FIGS. 6B and 6C depict one embodiment of a pulse oximetry probe 602 incorporating the shielded detector. FIGS. 6B and 6C also show the attachment of the probe 602 onto the fingertip 650 of an adult patient. As shown in FIG. 6B, the probe 602 is designed to fit comfortably onto a patient's fingertip. Advantageously, the probe is also designed to be disposable. Referring to FIG. 6B, the probe has a release liner 603, which is removed from the probe 602 to expose an adhesive surface 608 which adheres to the finger 650. The probe 602 includes a central portion 604, a pair of adhesive flanges 605 extending from the central portion 604, a connector portion 610 situated between the flanges 605, and a pair of smaller adhesive flaps 615 extending from the central portion 604 on the end of the probe 602 opposite from the connector 610. The probe 602 further includes a connection aperture 612 formed in the connector tab 610 and an emitter aperture 620 with a light-emitting diode (LED) emitter 670 (FIG. 6A). A flex pocket 625 is located within the central portion 604 between the emitter aperture 620 and a detector aperture 630. The probe 602 folds at the location of the flex pocket 625 over the fingertip 650. The detector aperture 630 allows light to pass through to a detector assembly 635 which contains a photodiode detector 500, as described above with respect to FIGS. 5A–5E. An adult fingertip 650 is shown in phantom in FIG. 6B to illustrate the position at which the fingertip 650 would be placed within the probe 602 prior to being fastened onto the fingertip 650 for use.

FIG. 6C illustrates the probe 602 fastened onto the fingertip 650. The probe 602 folds such that the flex pocket 625 aligns with the very end of the fingertip and such that adhesive flaps 605 fold downward (in the illustration of FIG. 6C) to wrap around the fingertip 650 while the adhesive flaps 615 fold upward (in the illustration of FIG. 6C) about a portion of the circumference of the fingertip 650 to provide support. When the probe 602 is folded about the fingertip 650, the emitter aperture 620 is spaced opposite the detector assembly 635 such that light from the emitter 670 (FIG. 6A) passes through the emitter aperture 620, through the finger 650 and is incident upon the detector assembly 635 through the detector aperture 630.

Figure 8:
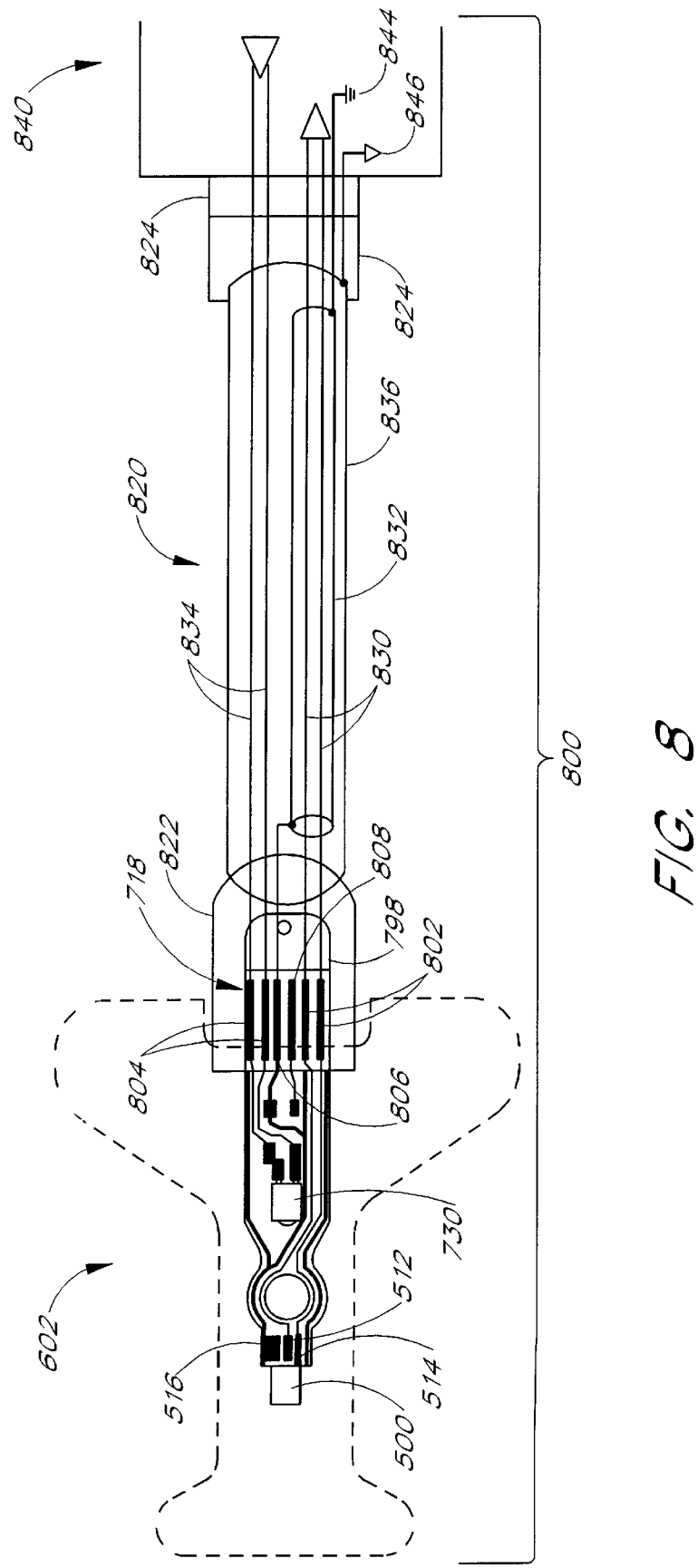
FIG. 8 is a schematic illustrating the interconnection of a pulse oximeter system utilizing a photodiode detector according to the present invention.

FIG. 6C depicts a receiving connector portion 660 (in phantom) which engages with contacts 652 on the connector 610 to provide an electrical connection between the probe 602 and signal processing circuitry within a pulse oximeter instrument 840 (FIG. 8). The digital signal processing circuitry may be used to analyze the output of the detector 500 (not shown) within the assembly 635. In one advantageous embodiment, the aperture 612 engages a tab (not shown) within the connector 660 to firmly secure the connector 660 to the probe 602. Once the probe 602 is securely fastened to the fingertip 650 and the connector provides an electrical connection between the probe 602 and the pulse oximeter, signals are detected from the detector 500 and transmitted to the signal processing circuitry via the connector 660.

FIGS. 7A–7C illustrate the assembly of the pulse oximetry probe depicted in FIGS. 6A–6C. The probe 602 is fabricated from multiple layers, including a flex circuit layer 710, a polyester shield layer 720, a face stock tape layer 794, a base stock layer 792 with the releasable liner 603 (FIG. 6B), and various pieces of pressure-sensitive adhesive (PSA).

Referring to FIG. 7A, a shielded flex circuit assembly 700 is formed from the flex circuit layer 710 located between folded portions of a flex circuit shield layer 720. The flex circuit shield layer 720 is advantageously constructed from polyester laminated with a thin conductive layer, such as copper. A preferred laminated polyester is made by TECHNIMET, part number SO-2010-1-3 and has an insulator film made by Coating Sciences, part number P-341. The insulator film prevents electrical contact between flex circuit traces and the conductive layer of the flex circuit shield layer 720.

A shielded detector 500 according to the present invention, which may have an integrated electromagnetic shield or an integrated ambient-light shield or both, is attached to the flex circuit 710. Each of the three detector leads, the cathode lead 512, the anode lead 514 and the shield lead 516, are soldered to one of three flex circuit solder pads. In one embodiment, an encapsulated emitter 730 containing red and infrared LEDs which are connected "back-to-back" so as to share two common leads is also attached to the flex circuit 710 by soldering each of these two leads to one of two flex circuit solder pads. Other emitter configurations are also possible, such as a three-lead emitter where the red and infrared LEDs share a common anode lead but have separate cathode leads or a four-lead emitter where the LEDs have no common leads.

In one embodiment, a resistor 740 is also attached to the flex circuit 710. The resistor leads are soldered to two flex circuit solder pads, connecting the resistor 740 in parallel to the emitter 730. This resistor value provides an identifier which specifies, for example, the intended patient type (adult, neonatal, etc.) or the probe manufacturer. The resistor value can be read by a pulse oximeter connected to the probe when a voltage is applied across the emitter 730 which is less than an LED threshold voltage, thereby effectively removing the LEDs from the circuit as a current load.

As further shown in FIG. 7A, the polyester shield layer 720 is laminated to the flex circuit 710 by a piece of conductive PSA 712 attached to the detector end of the flex circuit 710 and by pieces of nonconductive PSA 714, 716 attached, respectively, to the component and non-component sides of the emitter end of the flex circuit 710. The PSA strips bond the flex circuit shield layer 720 to both sides of the flex circuit 710 to provide a conductive EMI shield for the flex circuit 710 which covers all but the flex circuit contact fingers 718 and the optical path of the detector 500 and emitter 730, which remain exposed. The conductive PSA 712 provides an electrical connection between a folded portion 715 of the flex circuit 710 and an uninsulated portion 722 of the conductive flex circuit shield 720. The flex circuit folded portion 715, in turn, is part of a shield trace on the flex circuit which provides a low impedance path to both the detector shield lead 516 and to a shield contact portion of the contact fingers 718.

An optical cavity 750 is attached to the detector end of the flex circuit assembly 700 with a piece of PSA 752. The optical cavity 750 is made from styrene in one embodiment. In one preferred embodiment, the optical cavity 750 is coated with an optical coating that is opaque to ambient light. In an alternative embodiment, the optical cavity 750 can be made from a material that is opaque to ambient light. The optical cavity 750 has a rectangular receiving receptacle 754 adapted to receive the detector end of the flex circuit assembly 700. Advantageously, the optical cavity 750 has a wedge shape ramp 756 as part of the receptacle 754 which provides for a smooth transition for the flex circuit 710 between the surface of the base material 792, described below with respect to FIG. 7C, and the bottom surface of the receptacle 754. The walls of the receptacle 754 hold the flex circuit assembly 700 in position such that the attached detector aligns properly with an aperture 758 in the optical cavity 750. Preferably, the flex circuit assembly 700 fits snugly between the side walls and against the end wall. In a preferred embodiment, the optical cavity aperture 758 is configured to be cone-shaped, cylindrical or conical.

A cover 770 is placed over the optical cavity 750. The cover 770 is advantageously vacuum-formed and is cup-shaped. In a preferred embodiment, the cover 770 is made from polypropylene. A light barrier disk 760 is placed inside the cover 770 to block ambient light. Preferably, the disk 760 is made from a thin metal foil, such as aluminum foil. The cover 770 may also be made opaque to ambient light by applying a coating or by selecting a suitable construction material. The cover 770 has a flange 772 which serves as a bonding surface with the base material 792, described below. A connector tab 780 is attached to the emitter end of the flex circuit assembly 700 with a piece of PSA 782. The connector tab 780 is advantageously formed of ABS styrene and has an aperture 784.

FIG. 7B depicts the completed flex circuit assembly 700. As shown in FIG. 7C, the flex circuit assembly 700 is sandwiched between a base stock 792 and a face stock 794. In one embodiment, the base stock 792 comprises Avery 5051 base material and is transparent to the emitter wavelengths. The bottom side of the base stock 792 is coated with an acrylic PSA and is provided with a thin release layer 603, preferably made from a paper release liner or the like, as is well understood in the art. The top side of the base stock 792 is laminated with an unsupported rubber PSA, such as Coating Sciences U-224.

The face stock 794 is advantageously constructed from a non-woven, flexible material which is placed over the flex circuit assembly 700 and the base stock 792. In a preferred embodiment, the face stock 794 comprises Betham part number 1107-S. The face stock 794 preferably has an aperture 795 to allow the cup portion 774 of the cover 770 to protrude through the face stock 794. The face stock 794 covers the flange portion 772 of the cover 770. Because the base stock 792 has PSA on the side to which the face stock 794 is applied, pressure applied to the face stock 794 bonds the face stock with the base stock. The face stock 794 may also have PSA on the side which bonds to the base stock 792. The face stock 794 is cut such that the connector tab 780 and connector traces 718 remain exposed, forming a probe connector 798.

FIG. 8 schematically represents a pulse oximeter system 800, illustrating the cabling, interconnection and grounding for a pulse oximeter probe incorporating a photodiode with integrated noise shielding, as described above. The pulse oximeter system 800 comprises a probe 602 (described above) interconnected with a pulse oximeter instrument 840 via a patient cable 820. The cable 820 has a first connector 822 which mates with the probe connector 798. The cable 820 has a second connector 824 which mates with a pulse oximeter connector 842. An embodiment of the patient cable 820 comprises a pair of signal wires 830, an inner shield 832 surrounding the signal wires 830, a pair of drive wires 834 and an outer shield 836 surrounding the drive wires 834 and inner shield 832. In one embodiment, the probe connector 798 has six flex circuit connector traces 718. The anode lead 514 and cathode lead 512 of the detector 500 are connected to two of these traces 802, which mate to the double-shielded input wires 830 of the patient cable 820 via the first cable connector 822. The input wires 830 are brought into the pulse oximeter instrument 840 via the second cable connector 824 and the oximeter connector 842. The emitter 730 is also connected to two of the flex circuit connector traces 804, which mate to the outside-shielded drive wires 834 of the patient cable 820 and which are driven by the pulse oximeter instrument 840 via the oximeter connector 842 and the second cable connector 824. The integrated shield lead 516 of the detector 500 is connected to one of the flex circuit connector traces 806. In one embodiment, the shield trace 806 may be connected to the patient cable inner shield 832 which, in turn, may be connected to ground 844 within the pulse oximeter instrument 840 via the second cable connector 824 and the oximeter connector 842. In one embodiment, there is an unused probe trace 808, and the outer shield 836 of the patient cable 820 is not connected to the probe 602. The outer shield 836, however, may be grounded 846 at the pulse oximeter electronics 840 via the second cable connector 824 and the oximeter connector 842.

The integrated photodiode electromagnetic shield and ambient light shield and associated pulse oximeter probe have been disclosed in detail in connection with the preferred embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A shielded detector comprising:

a photodetector having an active area exposed to receive light and responsive to light within a band of wavelengths; and a shield deposited on a portion of said active area, said shield comprising an electrically conductive layer deposited on said portion of said active area, said shield providing an integrated electromagnetic shield for reducing EMI-induced noise in said photodetector, wherein said conductive layer comprises a metallization layer deposited directly on said portion of said active area to form said shield and an electrode for said photodetector, said electrode being substantially electrically isolated from said shield.

2. The shielded detector of claim 1, wherein said shield comprises a grid.

3. A shielded detector comprising:

a photodetector having an active area to receive light and responsive to light within a band of wavelengths; and a shield deposited on a portion of said active area, wherein said photodetector comprises a generally planar photodiode, said photodiode having first and second sides, said first side having said active area and said second side having a first electrode for said photodiode, wherein said shield comprises a metallization layer deposited directly on said portion of said active area, said metallization layer forming an electrically conductive grid and a second electrode for said photodiode, said second electrode being substantially electrically isolated from said grid.

4. The shielded detector of claim 3, further comprising a pad portion having a low impedance path to said grid, said grid forming an integrated electromagnetic shield, said pad adapted to be externally terminated through a conductor attached to said pad.

5. The shielded detector of claim 4, further comprising an optical filter material encapsulating said photodiode, said filter transmitting light of at least selected wavelengths within said band of wavelengths and attenuating at least some other wavelengths within said band.

* * * * *